CHRYSANTHEMUM PLANT
Filed Nov. 12, 1973
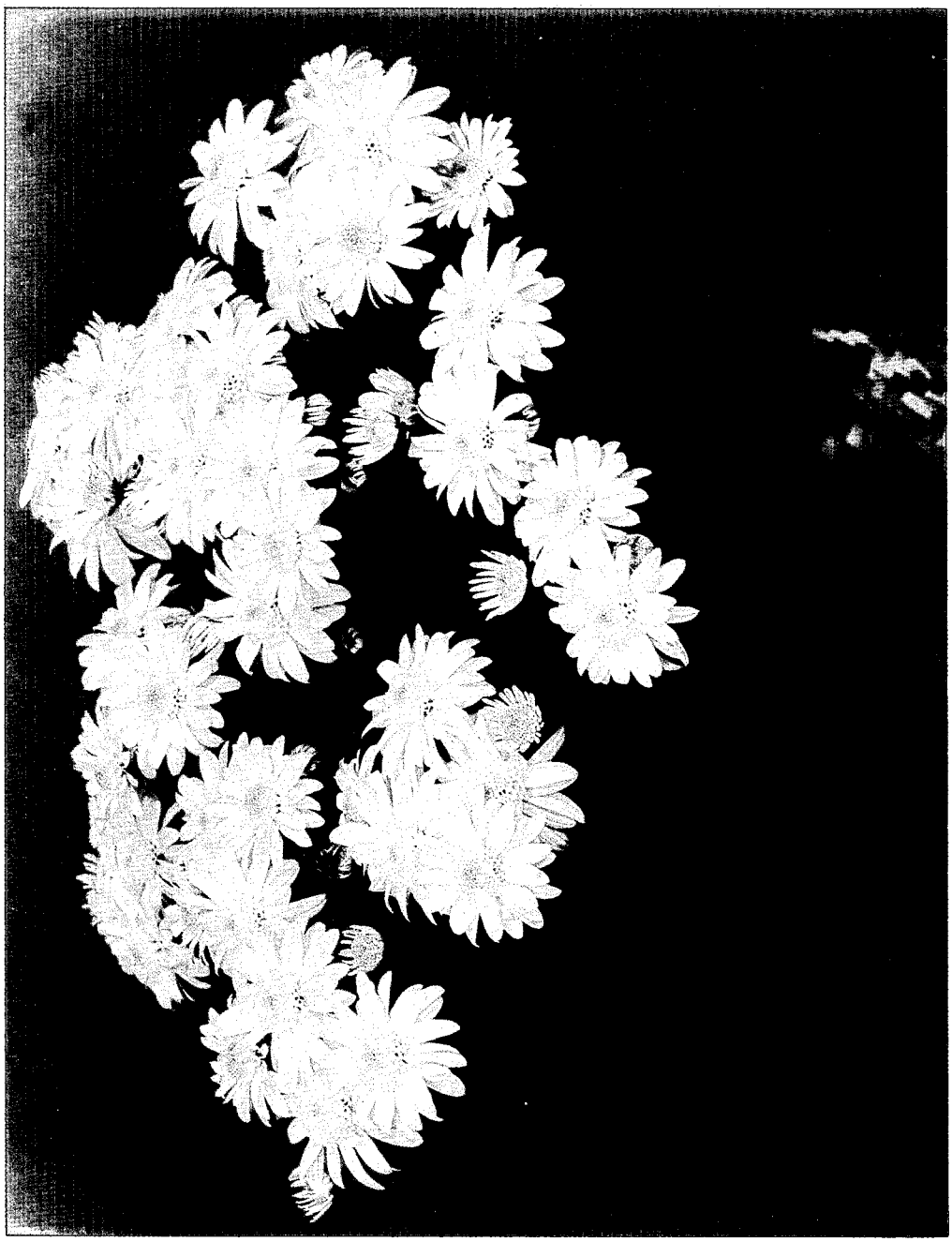

United States Patent Office

Plant Pat. 3,672

Patented Dec. 24, 1974

3,672

CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 12, 1973, Ser. No. 415,250

Int. Cl. A01h *5/00*

U.S. Cl. Plt.—74 1 Claim

The present invention comprises a new and distinct cultivar of chrysanthemum plant known by the varietal name Pioneer, which is a seedling of #67100–005 ×#21580–E01. Both parents are unpatented and identified for breeding purposes by the above breeding numbers.

The new cultivar uniquely contributes to the floriculture industry by its anemone flower form, yellow flower color, and by its reliable and uniform nine week response for tall treatment pot mum culture on a year around basis. Its unique anemone form is rarely seen in commercial pot chrysanthemums.

The new cultivar was selected from the progeny of the designated cross, and when asexually reproduced by cuttings at Barberton, Ohio, has been found to retain its distinctive characteristics through successive propagation.

The new cultivar, when grown in the vicinity of Barberton, Ohio, has a response period of approximately 9 weeks and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern, southeastern, southwestern United States, and coastal California is January through December, and in southern Florida under outdoor conditions, October through April.

The accompanying drawing shows the unique characteristics of the new cultivar, the color being as nearly true as possible with color illustrations of this type. Color references are made to the Munsell Book of Color, 1963 edition.

Botanical classification: *Chrysanthemum morifolium*, Ramat

| | |
|---|---|
| Bloom: | Pioneer |
| *Size* | 2½"–2¾". |
| *Fully expanded* | 3". |
| *Borne* | In terminal clusters on elongated branches. |
| *Stems* | Wiry. |
| *Form* | Anemone. |
| *Permanence* | 18–21 days. |
| *Color:* | |
| Center of flower | Yellow-green, 2.5GY6/8 to golden yellow, 3.75Y8/12. |
| Base of petals | Yellow-green, 2.5GY8/10. |
| Inside of petals | Clear yellow, 7.5Y8.5/12 to yellow, 7.5Y8.5/10. |
| Reverse of petals | Yellow, 7.5Y8.5/8 to light yellow, 7.5Y9/6. |
| Tonality from a distance | Clear yellow. |
| Discoloration | Yellow, 7.5Y8.5/10. |
| Petals: | |
| *Texture* | Smooth. |
| *Appearance and form* | Open at base, broad shallow multiridge keel, tapering to a sharp point. |
| *Arrangement* | Composite, whorled on a single receptacle. |
| *Persistence* | Resists shatter. |
| *Fragrance* | Typical chrysanthemum. |
| Reproductive organs: | |
| *Stamen, anthers* | 200+. |
| *Pollen* | Abundant to none. |
| *Arrangement* | Clustered in center of flower, if present. |
| *Styles* | Present both ray and disc florets. |
| *Length* | Short. |
| *Ovaries* | At the base of petal attached to receptacle. |
| Plant: | |
| *Form* | Herbaceous. |
| *Growth* | Semi-upright. |
| *Height* | Approximately 12"–15" when grown in a 4-cutting, 6" pot grown as a spray pot given one 2500 p.p.m. application of B–9 and timed as a 9 week tall treatment variety as defined in the timetables of Yoder Brothers, Inc., Barberton, Ohio, for the various seasons. |
| *Spread* | Approximately 8"–12" when grown in a 4-cutting, 6" pot grown as a spray pot given one 2500 p.p.m. application of B–9 and timed as a 9 week tall treatment variety as defined in the timetables of Yoder Brothers, Inc., Barberton, Ohio, for the various seasons. |
| Foliage: | |
| *Top side* | Dark Green, 7.5GY3/4. |
| *Size* | Length to width ratio 3:2 with length to 3¾" and width to 2½". |
| *Quantity* | Numerous. |
| *Shape* | Spatulate lobed. |
| *Texture* | Smooth. |
| *Ribs and veins* | Prominent. |
| *Edge* | Moderately indented. |
| *Serration* | Fine. |
| *Under side* | Medium green, 7.5GY5/4. |
| *Stipules* | Prominent. |

We claim:

1. A new and distinct cultivar of chrysanthemum characterized by its anemone form, yellow flower color, and by its reliable and uniform 9 week response for tall treatment pot mum culture on a year around basis.

No references cited.

ROBERT E. BAGWILL, Primary Examiner